United States Patent
Vakharia et al.

(10) Patent No.: US 8,021,363 B2
(45) Date of Patent: Sep. 20, 2011

(54) DUAL-BEND SPHINCTERTOME

(75) Inventors: Omar J. Vakharia, Cincinnati, OH (US); Rudolph H. Nobis, Mason, OH (US); Christopher Paul Swain, London (GB); Charles Alexander Mosse, London (GB); Keiichi Ikeda, Tokyo (JP)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1180 days.

(21) Appl. No.: 11/741,198

(22) Filed: Apr. 27, 2007

(65) Prior Publication Data
US 2007/0255299 A1  Nov. 1, 2007

Related U.S. Application Data

(60) Provisional application No. 60/746,086, filed on May 1, 2006.

(51) Int. Cl.
*A61B 18/14* (2006.01)
*A61B 17/32* (2006.01)

(52) U.S. Cl. ......................... 606/47; 606/113

(58) Field of Classification Search ............ 606/41, 606/113, 170, 45–50; 600/564
See application file for complete search history.

(56) References Cited

U.S. PATENT DOCUMENTS

| | | | |
|---|---|---|---|
| 3,910,279 A * | 10/1975 | Okada et al. ............... | 606/47 |
| 4,905,691 A * | 3/1990 | Rydell ......................... | 606/47 |
| 5,075,062 A | 12/1991 | Karpiel | |
| 5,810,807 A | 9/1998 | Ganz et al. | |
| 6,331,166 B1 * | 12/2001 | Burbank et al. ............. | 600/567 |
| 6,852,112 B2 * | 2/2005 | Platt ............................ | 606/49 |
| 7,824,342 B2 * | 11/2010 | Minosawa et al. .......... | 600/564 |
| 7,833,223 B2 | 11/2010 | Vakharia et al. | |
| 2003/0208219 A1 | 11/2003 | Aznoian et al. | |
| 2004/0199159 A1 * | 10/2004 | Lee et al. .................... | 606/47 |
| 2007/0185511 A1 * | 8/2007 | Minosawa et al. .......... | 606/170 |
| 2007/0255303 A1 | 11/2007 | Bakos et al. | |

FOREIGN PATENT DOCUMENTS

EP  0904796  3/1999

OTHER PUBLICATIONS

Hintze et al.,"Endoscopic Sphincterotomy Using an S-shaped Sphinctertome in Patients with a Billroth II or Roux-en-Y Gastrojejunostomy", Endoscopy, Feb. 1997, vol. 29(2): pp. 74-78.

* cited by examiner

*Primary Examiner* — Michael Peffley
*Assistant Examiner* — Samantha Good
(74) *Attorney, Agent, or Firm* — Nutter McClennen & Fish LLP

(57) ABSTRACT

Disclosed herein are devices and methods for forming multidirectional cuts in tissue. The tissue cutting devices disclosed herein generally include a flexible elongate member with at least first and second wires that are at least partially constrained within or along a portion of the member. A distal portion of the wires is anchored on or within a portion of the elongate member. When tension is applied to one of the wires, such as by an actuator at a proximal end of the device, the elongate member bows while an unconstrained portion of the wire becomes exposed relative to the adjacent portion of the elongate member, assuming a tissue-cutting configuration.

15 Claims, 7 Drawing Sheets

DUAL-BEND SPHINCTERTOME

REFERENCE TO RELATED APPLICATION

This application claims priority from U.S. Provisional Patent Application Ser. No. 60/746,086, filed on May 1, 2006, entitled "Dual-Bending Sphinctertome," which is expressly incorporated by reference herein.

FIELD OF THE INVENTION

The present invention relates to surgical cutting devices, and in particular to multidirectional cutting devices.

BACKGROUND OF THE INVENTION

Laparoscopic surgery is one type of minimally invasive surgery in which a surgeon uses numerous trocar ports to access a tissue site of interest within the abdominal cavity of a patient. The benefits of laparoscopic surgery, as compared to open incisional, abdominal surgery, include less pain, shorter recovery time, less scarring, and lower cost. Endoscopic surgery affords another way to access the abdominal cavity via natural openings (mouth, anus, vagina, urethra) of the body and through the peritoneal lining of the abdominal cavity. Obviously, the size and shape of instruments that may be passed through a body lumen in order to perform a medical procedure in the abdominal cavity are greatly restricted due to the anatomical properties of the lumen.

General surgeons, gastroenterologists, and other medical specialists routinely use flexible endoscopes for intralumenal examination and treatment of the upper gastrointestinal (GI) tract, via the mouth, and the lower GI tract, via the anus. In these procedures, the physician advances the flexible endoscope through the lumen, periodically pausing to articulate the distal end of the endoscope using external control knobs, to redirect the distal tip of the endoscope. In this way, the physician may navigate the tortuous passageway of the upper GI past the pharynx, through the esophagus and gastro esophageal junction, and into the stomach. The physician must take great care not to injure the delicate mucosal lining of the lumen, which generally may stretch open to a diameter in the range of about 15-25 mm, but normally has a non-circular cross sectional configuration when relaxed.

During such translumenal procedures, a puncture must be formed in the stomach wall or in the gastrointestinal tract to access the peritoneal cavity. One device often used to form such a puncture is a needle knife which is inserted through the working channel of the endoscope, and which utilizes energy to penetrate through the tissue. A sphinctertome can then be inserted and reinserted into the tissue to expand the puncture made by the needle knife to form a multidirectional incision in the tissue. While effective, such a procedure for forming multidirectional incisions in tissue is time consuming and can also cause unnecessary distress to the tissue.

Accordingly, there remains a need for improved surgical cutting devices.

SUMMARY OF THE INVENTION

The present invention provides various devices and methods for forming a cut in tissue. In one aspect, a device for cutting tissue is provided that includes a flexible elongate member and a first tissue cutting wire that extends along the member. The first tissue cutting wire can have a first portion that is constrained with respect to the member, a distal portion that is anchored to the member, and an unconstrained portion that is adjacent to a first bend region on the member. The device can also include a second tissue cutting wire that extends along the member and which has a first portion that is constrained with respect to the member, a distal portion that is anchored to the member, and an unconstrained portion that is adjacent to a second bend region on the member. The unconstrained portions of the first and second wires can be adapted to move from a delivery configuration to a cutting configuration to effect cutting of tissue upon the selective application of tension the wires.

The wires can have a variety of orientations with respect to the member to effect formation of a multidirectional cut. In one embodiment, the unconstrained portion of the first wire can be spaced longitudinally apart from the unconstrained portion of the second wire. Additionally or alternatively, the unconstrained portions of the first and second wires can be circumferentially spaced from one another about the member.

The first portions of the wires can be constrained and the distal portions of the wires anchored using a variety of techniques. In one embodiment, the wires can be constrained within and anchored to lumens or guide channels formed in the elongate member. In another embodiment, the wires can be constrained and anchored by a plurality of spaced retaining members positioned on the member. Additionally, the distal portions of the wires can be anchored to the member at a position that is offset from a longitudinal axis of the member to facilitate bending of the member.

The device can also include a variety of other features, such as a central working channel that extends between the proximal and distal ends of the member. The central working channel can have an incising element disposed therein and/or can be adapted to receive a guide device or an incising element.

In another aspect, a device for cutting tissue can include a flexible elongate member having proximal and distal ends, a first guide channel extending along a portion of the member, and a second guide channel extending along a portion of the member and angularly spaced along a circumference of the member relative to the first guide channel. The first guide channel can include a first tissue-cutting wire that has a proximal end slidably disposed therein and an exposed portion that extends distally beyond the first guide channel. Similarly, the second guide channel can include a second tissue-cutting wire having a proximal end slidably disposed therein and an exposed portion that extends distally beyond the second guide channel. The device can also include an actuator coupled to the proximal ends of the first and second wires. The actuator can be adapted to selectively apply tension to the first and second wires that is effective to bend the member and expose a portion of the wire which extends distally beyond the guide channels to cause the device to assume a cutting configuration in which one or both of the wires is exposed relative to the member.

The exposed portions of the first and second tissue-cutting wires can be positioned at a variety of locations on the member. For example, the exposed portion of the first tissue-cutting wire can be longitudinally and/or circumferentially spaced a distance apart from the exposed portion of the second tissue-cutting wire along the member, or alternatively, the exposed portions of the first and second tissue-cutting wires can be at the same longitudinal position but circumferentially spaced along the member.

The guide channels can have a variety of configurations, and in one embodiment the guide channels can be lumens that are formed in or along the flexible elongate member. In another embodiment, the guide channels can be formed from a plurality of spaced retaining members located on the elongate member. The device can also include a variety of other features to facilitate cutting tissue, such as at least one central working channel that extends between the proximal and distal ends of the member. The central working channel can be adapted to have an incising element movably disposed therein and/or to receive a guide device or incising element.

Methods for cutting tissue are also provided. In one aspect, a method for cutting tissue can include inserting a selectively bendable, elongate flexible cutting member into a lumen of a body. The member can have a plurality of tissue-cutting wires extending therealong, and the plurality of wires can be at least partially exposed with respect to the member. The method can further include selectively applying tension to one of the plurality of wires to cause the member to bend adjacent to the exposed portion of the wire thereby separating the wire from the member so that it assumes a tissue-cutting orientation. Energy can be delivered to the wire when it is in the tissue-cutting orientation to effect cutting of a tissue.

For example, and in one embodiment, tension can be selectively applied to a first of the plurality of wires. This causes the member to bend in a first direction to separate a first tissue-cutting wire segment from the member such that the wire segment is in a position to form a cut in tissue. Thereafter tension can be selectively applied to a second of the plurality of wires to cause the member to bend in a second direction to separate a second tissue-cutting wire segment. In this position, the second wire segment can then form a second cut in the tissue, and the second cut can be formed in a different direction than the first cut. When the first tissue-cutting wire segment is positioned distal to the second tissue-cutting wire segment, the method can further include moving the member distally within the tissue to position the second tissue-cutting wire segment at the tissue to effect cutting.

The method can also include a variety of other steps to facilitate the formation of a cut in tissue, such as forming an incision in the tissue prior to the insertion of the member using an incising element disposed within a central working channel of the member or controlling an amount of tension applied to the wires such that the device can be positioned at a desired location in tissue. Additionally or alternatively, the method can include using a guidewire to position the member within the tissue.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
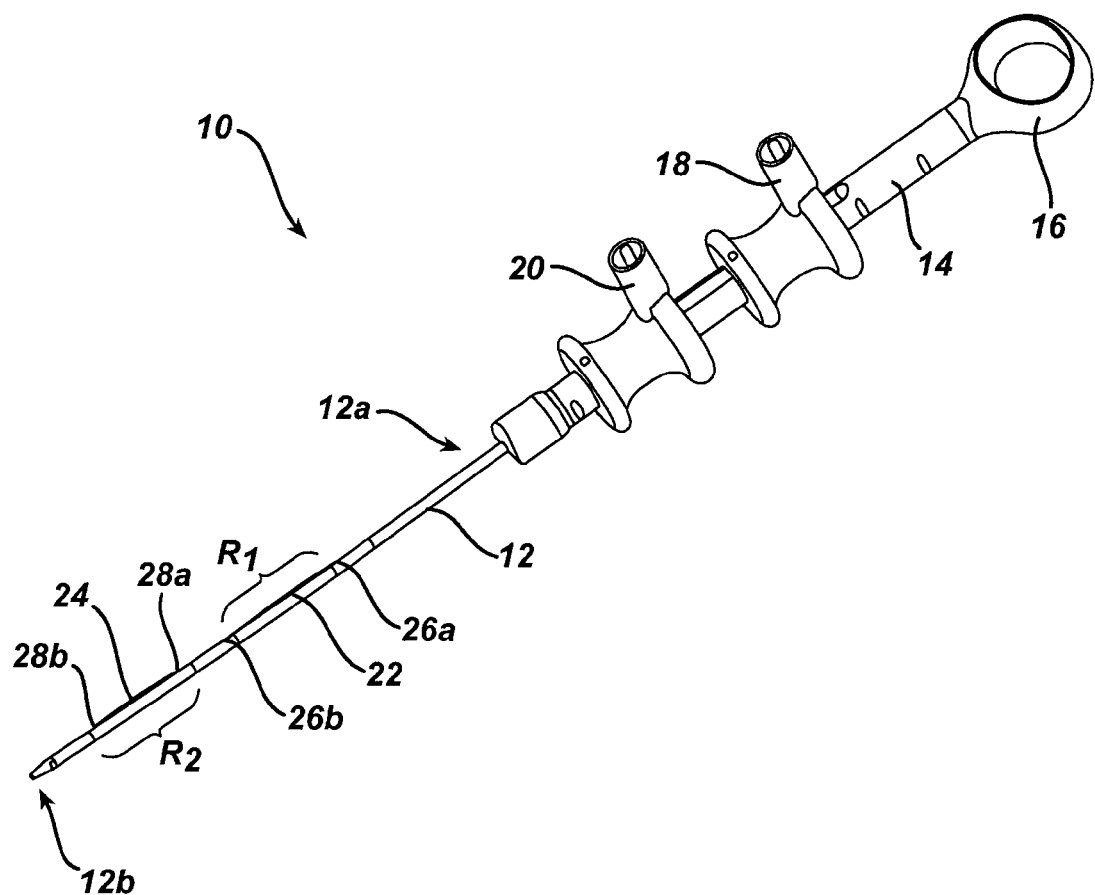
FIG. 1A is a perspective view of one embodiment of a surgical cutting device in a delivery configuration.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides devices and methods that can be used to form multidirectional cuts in tissue, such as bidirectional cuts. The tissue cutting devices disclosed herein generally include a flexible elongate member with at least first and second wires that are at least partially constrained within or along a portion of the member. A distal portion of the wires is anchored on or within a portion of the elongate member. When tension is applied to one of the wires, such as by an actuator at a proximal end of the device, the elongate member bows while an unconstrained portion of the wire becomes spaced from and exposed relative to the adjacent portion of the elongate member, assuming a tissue-cutting configuration.

Such a device is useful, for example, in transgastric surgical procedures where it is necessary to form incisions in tough stomach tissue. After puncturing the tissue, for example using a needle knife that can be integrated with or separate from the elongate member, the elongate member is advanced through the puncture to a desired position. The elongate member can then be oriented in the cutting configuration, and energy can be applied to the exposed wire to form a cut in tissue. The device can then be manipulated within the tissue (e.g., advanced further) and tension can be applied to another wire. This causes the elongate member to bend in a different direction and expose a different wire in a different cutting configuration that is effective to cut tissue in a different direction. A second cut can then be formed in the tissue in a direction that is different from the first cut. One skilled in the art will appreciate that while the tissue cutting devices disclosed herein are described primarily in the context of transgastric surgeries, they are applicable to a variety of surgical procedures, including intestinal surgeries to remove polyps and/or cancer treatment procedures.

FIGS. 1A-1E illustrate one embodiment of a device 10 for forming a bidirectional cut in tissue. As shown, the device 10 includes a flexible elongate member 12 having proximal and distal ends 12a, 12b and first and second guide channels 30, 32 that extend along at least a portion of the member 12 and house first and second tissue-cutting wires 22, 24. The wires 22, 24 each have first portions that can be constrained within the guide channels 30, 32 and distal portions that can be anchored within the guide channels 30, 32. Each wire 22, 24 also has an unconstrained portion that extends outside of the guide channels 30, 32. The unconstrained portion of the wires 22, 24 can be recessed within grooves (such as groove 36 shown in FIG. 1E) formed on the member 12 when the device 10 is in the delivery configuration. In use, tension can selectively and individually be applied to the wires 22, 24 to cause the wires 22, 24 to sequentially or simultaneously move from the delivery configuration the tissue-cutting configuration to effect the cutting of tissue.

Figure 1B:
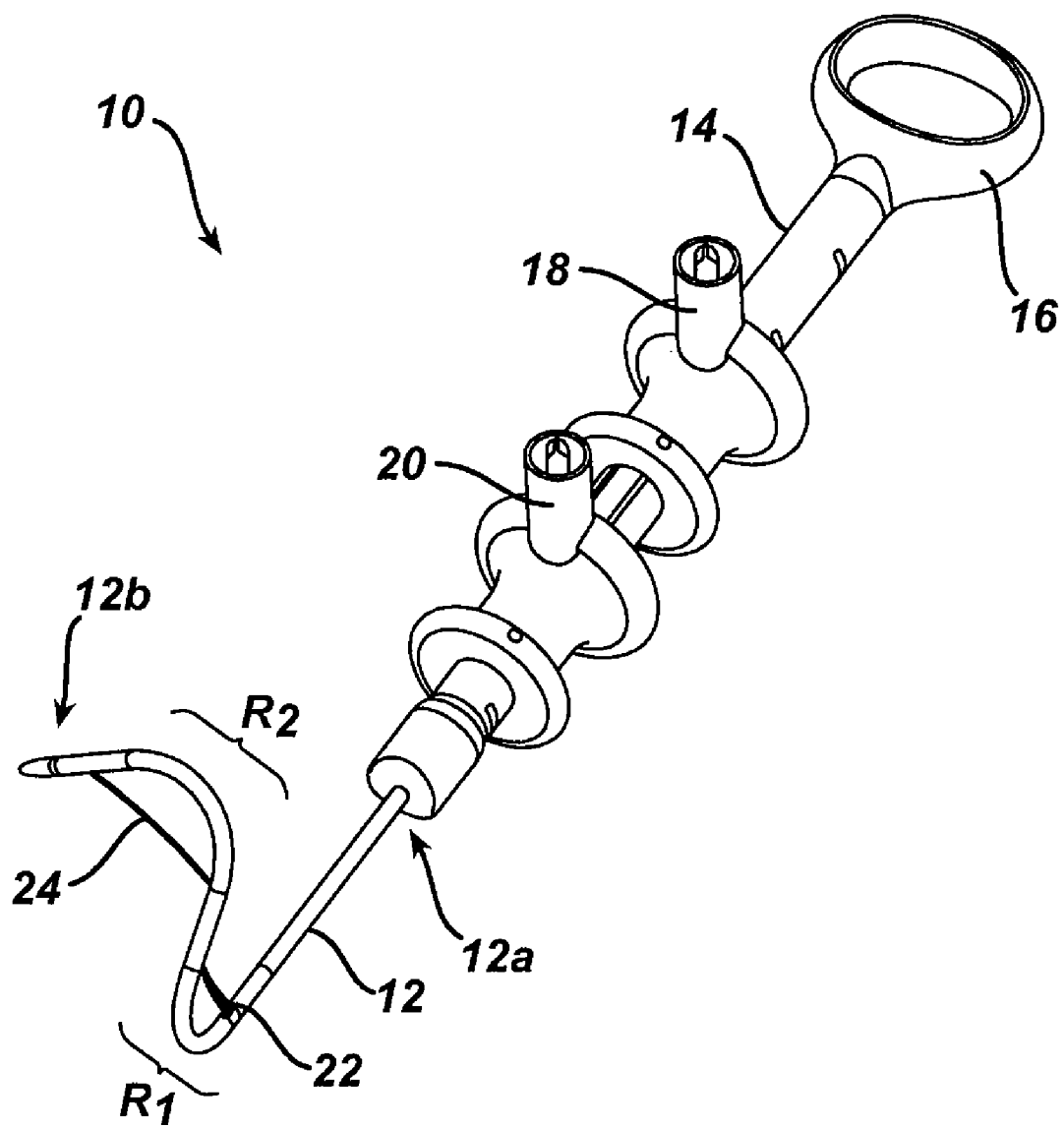
FIG. 1B is a perspective view of the device of FIG. 1A in a cutting configuration.
Figure 1C:
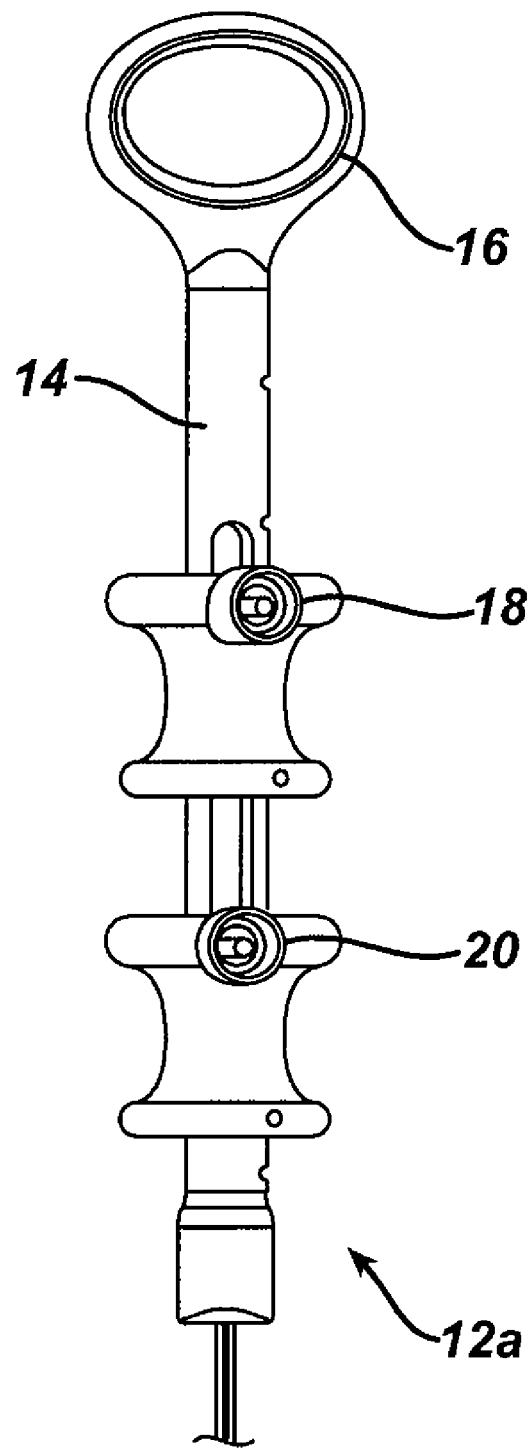
FIG. 1C is a front view of a handle of the device of FIG. 1B.
Figure 2A:
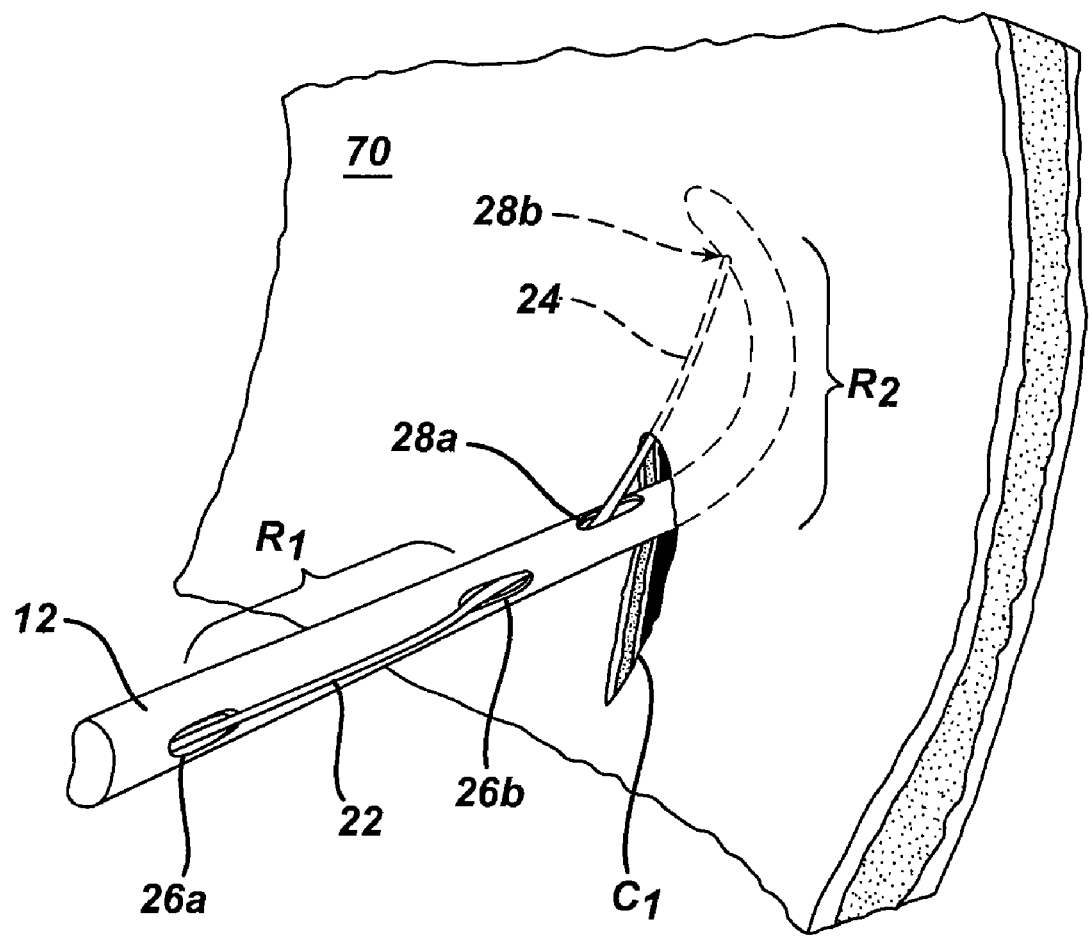
FIG. 2A is a schematic illustrating the device of FIG. 1A forming a first cut in tissue.
Figure 2B:
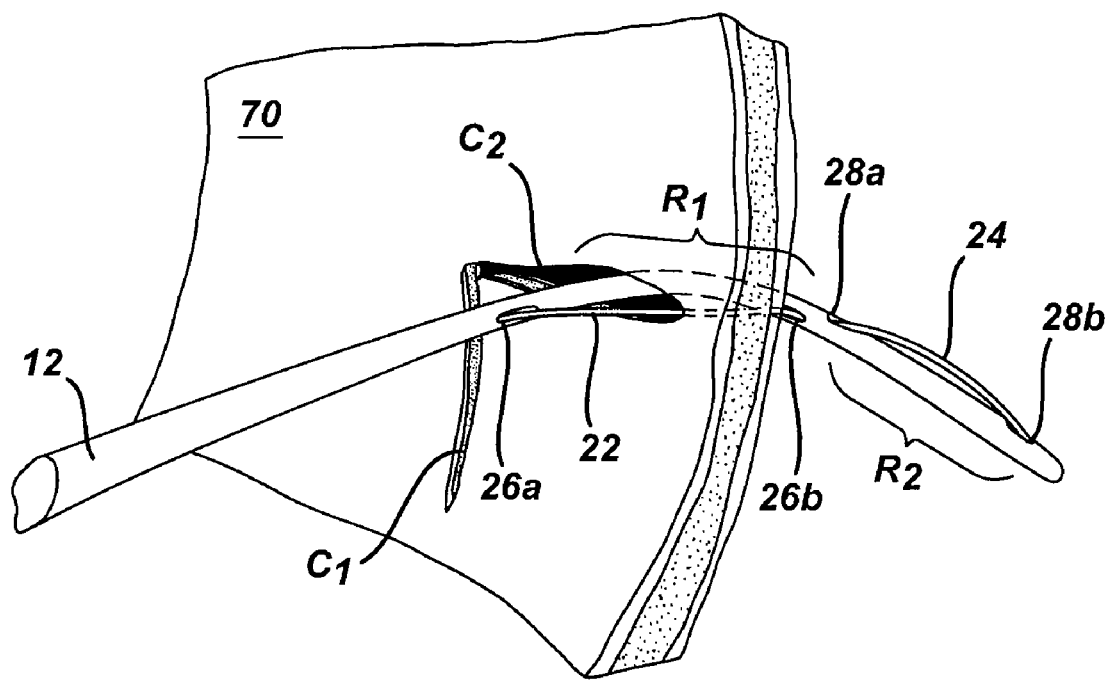
FIG. 2B is a schematic illustrating the device of FIG. 1A forming a second cut in tissue.

FIG. 1A illustrates the device 10 in the delivery configuration, in which the member 12 has a relatively straight or linear configuration and the unconstrained portions of the wires 22, 24 are located adjacent to and in close proximity to the member 12. The unconstrained portions of the wires 22, 24 can also rest within the grooves 36 that form recesses on the member 12 to facilitate ease of delivery to the target site in the tissue. Following the placement of the device 10 within tissue, the wires 22, 24 can be selectively and individually tensioned to move from the delivery configuration to the tissue cutting configuration. As a result of such application of tension to the wires 22, 24, as shown in FIG. 1B, a region $R_1$, $R_2$ of the member 12 bends and the wires 22, 24 are pulled out of the grooves such that they are positioned a distance away from the member 12 in a cutting configuration. Once the wires 22, 24 are exposed and separated from the member 12 in the cutting configuration, energy can be applied to the wires 22, 24 and the wires 22, 24 can be placed against tissue to cut it in a desired pattern. Although FIG. 1B illustrates bends in both regions $R_1$ and $R_2$ formed simultaneously, one skilled in the art will appreciate that the bends in regions $R_1$ and $R_2$ can also be formed sequentially as shown in FIGS. 2A-2B, as will be discussed in more detail below.

Figure 1D:
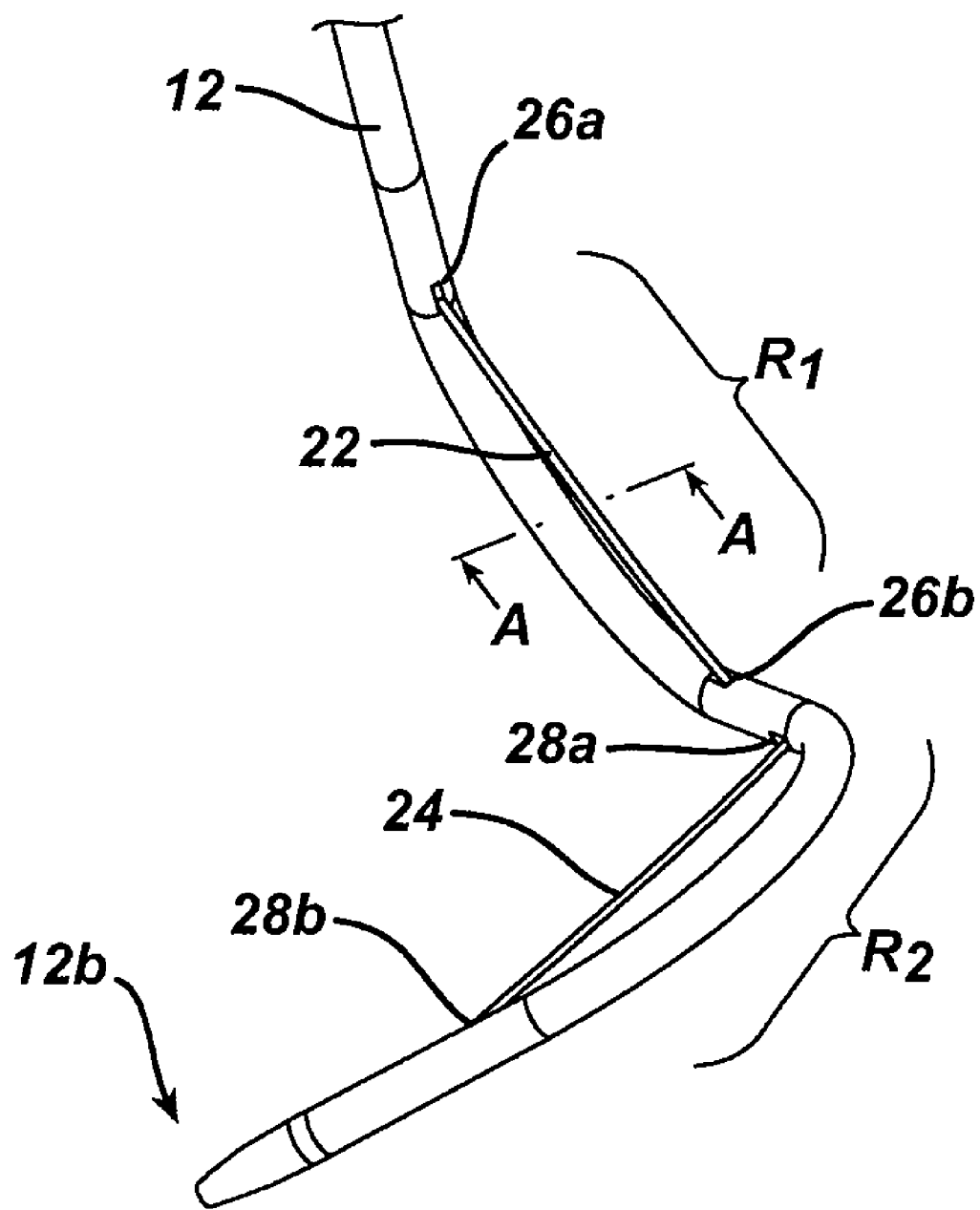
FIG. 1D is a perspective view of a distal end of a member of the device of FIG. 1B.

The flexible elongate member 12 can have virtually any configuration that allows it to be laparoscopically or endoscopically inserted to a surgical site. As shown, the member 12 is substantially cylindrical and sufficiently strong to be inserted into tissue, yet flexible enough to bend upon the application of tension to the wires 22, 24. The member 12 can include openings (openings 26a, 26b, 28a, 28b are shown in FIG. 1D) that correspond to openings in the guide channels 30, 32 to allow a portion of the wires 22, 24 to exit and reenter the guide channels 30, 32 and the member 12, such that they are unconstrained from the guide channels 30, 32. The member 12 can also include a groove or other receiver (groove 36 is shown in FIG. 1D) that is formed in the outer surface of the member 12 between the openings 26a, 26b, 28a, 28b. The grooves can be adapted to hold the unconstrained portions of the wires 22, 24 adjacent to the member 12 in a recessed condition when the device 10, or at least a portion thereof, is in a delivery configuration. This is particularly advantageous in that it protects the wires 22, 24 and tissue from damage during insertion of the device 10. The distal end 12b of the elongate member 12 can be adapted to facilitate insertion into tissue, and as shown in FIGS. 1A-1B and 1D, the distal end 12b can be tapered and/or rounded. Alternatively or additionally, the distal end 12b of the member 12 can include markings (not shown) formed thereon to facilitate positioning of the device 10 within tissue. While the member 12 can have a variety of sizes, and the size of the member 12 can depend upon the application of the device 10 and the type of tissue to be cut, in an exemplary embodiment, the member 12 can have a diameter in the range of about 2.0 mm to 3.5 mm, and more preferably about 2.4 mm.

Figure 1E:
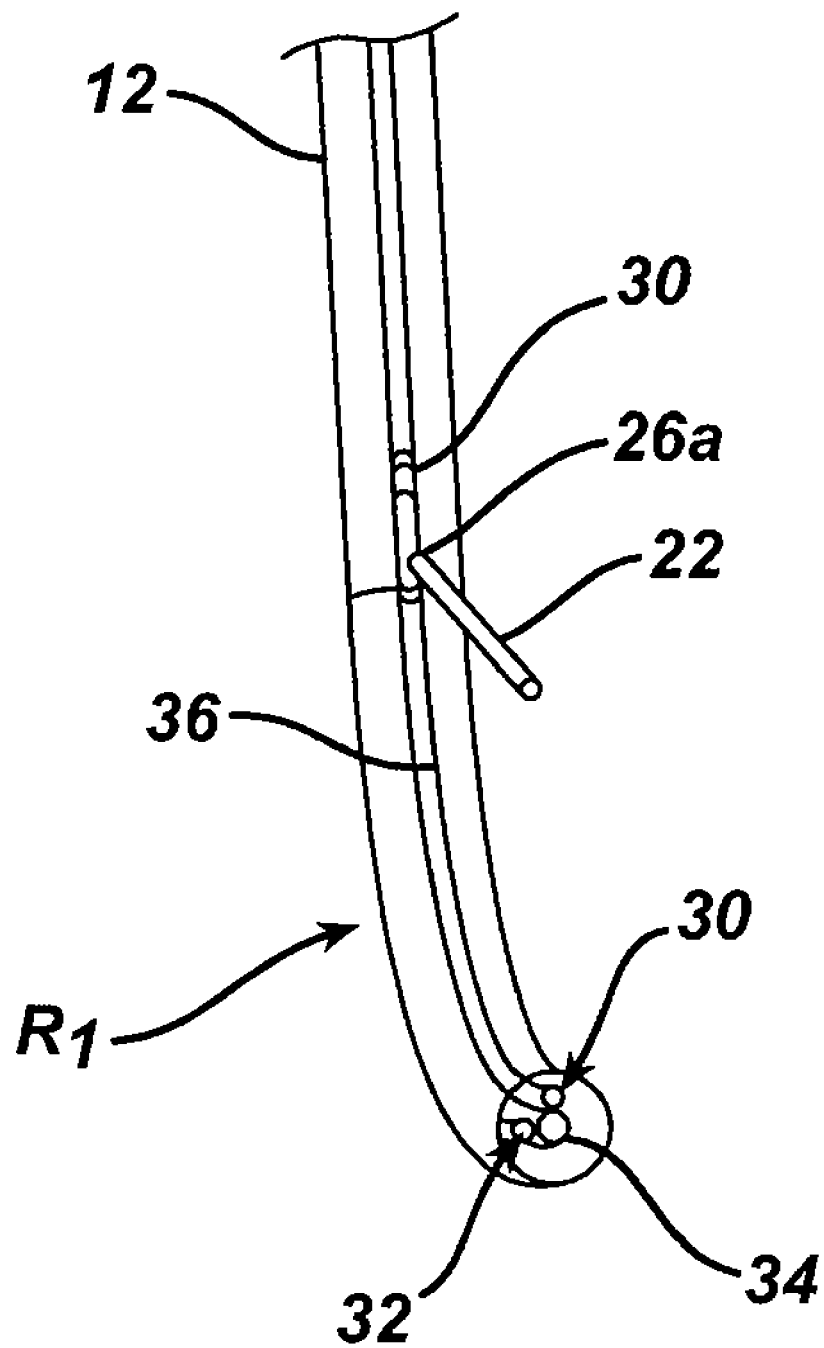
FIG. 1E is a cross-sectional view of a mid-portion of the member of the device of FIG. 1B taken across line A-A.

One skilled in the art will appreciate that the device 10 can also include a variety of features to facilitate the formation of a cut in the tissue. As shown in FIG. 1E, the member 12 can include at least one working channel 34 that can be centrally positioned and that extends therethrough. The working channel 34 can be adapted to hold a guide device, such as a guidewire, to facilitate positioning of the device 10 within tissue. Optionally or additionally, the working channel 34 can house an incising element (not shown) for forming an initial incision within the tissue. One skilled in the art will appreciate that the incising element can have a variety of configurations and can be integrated within the working channel or it can be a separate device that is inserted within the working channel. One exemplary incising element that can be used with the devices disclosed herein is the incising element employed in the integrated guidewire needle knife that is disclosed in commonly owned application entitled "Integrated Guidewire Needle Knife," filed concurrently herewith, the disclosure of which is incorporated by reference herein.

Referring back to FIGS. 1A-1C, a handle 14 can be located on the proximal end 12a of the member 12 to facilitate manipulation and handling of the device 10. The handle 14 can have any configuration that allows a user to conveniently hold and operate the device 10. In one embodiment however, the handle 14 has a substantially elongate shape and includes a thumb ring 16 to facilitate grasping. The handle 14 can also include at least one actuator that enables tension to be selectively applied to the tissue-cutting wires 22, 24. In one embodiment shown in FIG. 1C, the handle 14 includes first and second sliding actuator levers 18, 20 that are coupled to the first and second wires 22, 24, respectively. In alternate embodiments, rotatable knobs or dials can be used to selectively apply tension to the wires. A locking mechanism (not shown) can also be associated with the tension applying mechanism to hold the wires 22, 24 in position once tension is applied. In use, the levers 18, 20 can be moved in the proximal direction to apply tension to the wires 22, 24, causing the wires 22, 24 and the member 12 move from a delivery configuration to a tissue-cutting configuration. Once in the tissue-cutting configuration, the wires 22, 24 can be locked in position using the locking mechanism.

While a variety of locking mechanisms can be used, one exemplary locking mechanism can include a clamp that is effective to clamp down onto the wires and thereby prevent movement of the wires such that the device is held in the desired orientation. The clamp can have a variety of shapes and sizes, and it can be positioned at various locations on the device. In one embodiment, the clamp can be disposed within the handle. In an initial position, the clamp is spaced apart from the wires to allow free movement thereof. Once the wires are tensioned and the bend regions bent, the clamp can be moved until it engages the wires within the handle. The clamp will thus prevent movement of the wires when the clamp is in the locked position. In order to lock the clamp, the clamp can include a mating element formed thereon and configured to engage a corresponding mating element formed in the handle. For example, the clamp can include threads formed therein that are configured to mate with corresponding threads in the handle. As a result, rotation of the clamp about the handle will cause the clamp to move between the initial and locked positions. While the exemplary mating technique includes threads, one skilled in the art will appreciate that various other mating techniques can be used.

The handle 14 can also optionally be adapted to facilitate the delivery of energy to the wires 22, 24 to cut tissue. An energy source (not shown), such as a battery that is in electrical communication with the wires, can be disposed within the handle. Alternatively, the handle can be adapted to be coupled to an external energy source, such as a generator or an outlet. The handle can also include a mechanism that facilitates the selective delivery of energy to the wires, such as a button or knob that can cause activation of the energy source. While the exemplary embodiment illustrates an elongate handle 14, one skilled in the art will appreciate that the handle can have any configuration that allows a user to selectively apply tension as well as energy to the wires, such as a joystick control.

As noted above, first and second guide channels 30, 32 extend along at least a portion of the member 12 for constraining portions of the wires 22, 24 relative to the member 12. The guide channels 30, 32 can extend along the member 12 in a variety of orientations to help effect multidirectional bending of the device, however as shown, the guide channels 30, 32 are circumferentially spaced along the member 12. The circumferential spacing of the guide channels 30, 32, and hence the wires 22, 24, enables the bidirectional bending of the member 12. This circumferential spacing of the guide channels 30, 32 can result in an angular offset by a range of degrees to enable bidirectional bending of the member 12. As a result, the member 12 has two bend zones $R_1$, $R_2$ that are longitudinally separated and radially offset with respect to one another. This configuration, as will be described below, enables the device 10 to be inserted into tissue at a first distance, and then configured into a cutting configuration to form a cut in one direction using wire 24. The member 12 can then be advanced further within the tissue, and configured in a cutting configuration to cut tissue in another direction with wire 22.

The circumferential spacing of the guide channels 30, 32, and hence the wires 22, 24, also influences the shape of the resulting cut. By way of example, when the guide channels 30, 32 are angularly offset by about 90°, the bend regions $R_1$, $R_2$ can be located in planes that are perpendicular to one another to effect the formation of a substantially L-shaped cut. Alternatively, when the guide channels 30, 32 are angularly offset by about 180°, the bend regions $R_1$, $R_2$ can form a substantially S-shaped configuration, resulting in a substantially S-shaped cut.

In particular, and as shown in FIGS. 1A and 1D-1E, guide channel 30 extends though a portion of the member 12 to an opening 26a. At that point, wire 22, which is housed within the guide channel 30, emerges from the guide channel 30 and continues along the member 12, adjacent to the bend region $R_1$, when in an unconstrained condition. Distal to the bend region $R_1$, the wire 22 can re-renter the guide channel 30 through an opening 26b. Optionally, the wire 22 can be anchored at or just within the opening 26b, or it can extend further within the guide channel 30 to a securement point (not shown). Similarly, guide channel 32 also extends within the member 12 and, as shown in FIG. 1E, it is circumferentially spaced and angularly offset from the guide channel 30. Guide channel 32 can extend a greater distance within member 12 to an opening 28a, which is distal to openings 26a and 26b. Wire 24, which is housed within guide channel 32, emerges from the opening 28a and continues along the member 12, adjacent to the bend region $R_2$, when in an unconstrained condition. Distal to the bend region $R_2$, the wire 24 can re-enter the guide channel 32 through an opening 28b. The wire 24 can be anchored at or just within the opening 28b or it can extend further within the guide channel 32 to a securement point (not shown). While the exemplary embodiment illustrates guide channels 30, 32 that are longitudinally separated and radially offset with respect to one another, in other embodiments the guide channels can be spaced at the same longitudinal position and about the member at a variety of angles, such as, for example, about 180° relative to one another.

The guide channels 30, 32 can have a variety of configurations, however as shown in FIG. 1E, the first and second guide channels 30, 32 are lumens. In other embodiments, however, the guide channels can be retaining members, such as guides, clips, or fasteners, that are located on the outside of the member. The retaining members can be relatively closely spaced to hold the wires in a constrained position and more widely spaced to form the unconstrained portion of the wires.

As noted above, a distal portion of each of the wires 22, 24 is anchored to the member 12, for example, within a distal portion of its respective guide channel 30, 32. A variety of techniques can be used to anchor the distal portions of the wires 22, 24, such as welding, knots, adhesives, or other fasteners. In one embodiment, the inside of the guide channels can include hooks or some other fastener, and the distal end of the wires can be attached to such hooks or fasteners.

The distal ends of the wires 22, 24 can also be anchored within the guide channels 30, 32 at a position that is offset from the longitudinal axis of the member 12. As a result, and upon the application of tension to the wires 22, 24, the wires 22, 24 can act as a lever arm to facilitate bending of the member 12. The proximal ends of each of the wires 22, 24 can be disposed within the guide channels 30, 32 and coupled to a tension applying mechanism, such as the actuation levers 18, 20 located on the handle 14 as described above. A proximal portion of the wires 22, 24 can also be in electrical communication with, for example, a source of RF energy.

The wires 22, 24 can be formed from a variety of materials that are suitable to cut tissue. In one embodiment, the wires 22, 24 are made from a conductive material such that the tissue can be cut via electrosurgical energy. Exemplary materials can include stainless steel, nitinol, carbon steel, aluminum, and combinations thereof. One skilled in the art will appreciate that the wires can also have a variety of sizes depending upon the type of tissue to be cut. In one embodiment, however, the wires can have a diameter in the range of about 0.005 inch to 0.025 inch, and more preferably about 0.015 inch.

While the exemplary embodiment illustrates a device 10 having two wires 22, 24, one skilled in the art will appreciate that the device can have any number of wires in any number of configurations to form a variety of multidirectional cuts in tissue.

The device disclosed herein can be used in surgical procedures in the manner described below. Following preparation of the patient as known in the art, the member can be inserted into a natural or created orifice to a target site. As noted above, the device 10 is typically inserted in the delivery configuration shown in FIG. 1A, where the member 12 has a substantially linear configuration and the wires 22, 24 are located adjacent to the member 12 and optionally recessed within the grooves 36. A variety of techniques can be used to insert the device into the orifice, and in one embodiment a guide device, such as a guidewire, can be positioned within a central working channel of the device and used to guide the device to the target site. Once at the target site, the guide device can be removed from the working channel and optionally replaced by an incising element. Alternatively, in embodiments where the device includes an additional working channel for a treatment device, the incising element can be inserted in such a working channel while the guide device remains in place. In either embodiment, the cutting device can then be used to form an initial perforation in the tissue. A variety of incising elements can be used, however in one exemplary embodiment an integrated guidewire needle knife device can be used, such as that disclosed in commonly owned application entitled "Integrated Guidewire Needle Knife," filed concurrently herewith, the disclosure of which is incorporated by referenced herein.

Following the formation of the initial perforation, the device can be further advanced through the perforation so that an exposed portion of a wire to be used to cut tissue is properly positioned adjacent to the tissue to be cut. Thereafter, the member is moved to the cutting configuration. This can be effected by applying tension to one or more of the wires, which causes the portion of the member that is adjacent to the unconstrained portion of the wire to bend or bow, such that the unconstrained portion of the wire moves from a position adjacent to the member to a position spaced a distance away from the member and in a cutting configuration. For example, FIG. 2A illustrates the device 10 where tension is applied to wire 24 such that the bend region $R_2$ is bowed and the wire 24 is in a cutting configuration. In alternate embodiments, tension is simultaneously applied to the wires 22, 24 such that bend regions $R_1$, $R_2$ are bowed and the wires 22, 24 are in the cutting configuration, as shown in FIG. 1B. Once the wire is positioned in the cutting configuration, the locking mechanism can optionally be activated to maintain the position of the wire.

At this point, energy, such as RF energy, can be delivered to the tensioned wire by, for example, using an energy delivery mechanism on the handle. This causes the wire to penetrate the tissue, forming a cut in the tissue. For example, FIG. 2A illustrates the device 10 being used to form a first cut $C_1$ in tissue 70 using wire 24. Following the formation of the cut, the energy delivery can cease, and the locking member can optionally be released, causing the member to return to its delivery configuration. The device can then be further manipulated within the tissue to form a second cut, and optionally a third cut, in the tissue.

Once the first cut is made, the member can be further advanced into tissue so that another wire, e.g., wire 22, is adjacent to the tissue to be cut. Tension can then be applied to the wire 22, if the wire 22 is not tensioned already, causing a portion of the member $R_1$ that is adjacent to the unconstrained portion of the wire 22 to bend while the wire 22 becomes spaced a distance away from the member 12. Once the wire 22 is in this tissue-cutting configuration, energy can be delivered to the wire 22 to cause the wire 22 to penetrate the tissue 70 and form a second cut $C_2$, as shown in FIG. 2B. The second cut $C_2$ can have an different direction than the first cut $C_1$. For example, the second cut $C_2$ can be orientated at an angle (e.g., about 90°) relative to the first cut $C_1$ to form a substantially L-shaped cut. Such a device is particularly advantageous in that it can cut in multiple directions without the need to remove and reposition the device in the tissue.

Although the above methods use the sequential tensioning of the wires to form a multidirectional cut in tissue, one skilled in the art will appreciate that the wires can also be simultaneously tensioned and energy applied to one of the tensioned wires to form a cut in tissue. The simultaneous tensioning of the wires is particularly advantageous in that can facilitate positioning the device in tissue. For example, and referring back to FIG. 2B, as energy is applied to the wire 22, tension can be selectively applied to the wire 24. This keeps the device 10 from rotating to the original plane cut $C_1$ when other wires (wire 24) are positioned within tissue 70 to form a cut.

Cutting devices, including components thereof, can be designed to be disposed after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. By way of example, the devices disclosed herein can be reconditioned after the device has been used in a medical procedure. The device can be disassembled, and any number of the particular pieces (e.g., the wires, the member, or the handle) can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a cutting device can utilize a variety of techniques for disassembly, cleaning/replacement, and reassembly. Use of such techniques, and the resulting reconditioned cutting device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A device for cutting tissue, comprising:
   a flexible elongate member;
   a first tissue cutting wire extending along the member having a first constrained portion with respect to the member, a distal portion anchored to the member, and an unconstrained portion that is adjacent to a first bend region on the member; and
   a second tissue cutting wire extending along the member having a first constrained portion with respect to the member, a distal portion anchored to the member, and an unconstrained portion that is adjacent to a second bend region on the member,
   wherein a proximal end of the first tissue cutting wire is located distal to a distal end of the second tissue cutting wire along a length of the member;
   wherein the unconstrained portions of the first and second wires are adapted to be selectively tensioned to move from a delivery configuration to a cutting configuration to effect cutting of tissue.

2. The device of claim 1, wherein the unconstrained portion of the first wire is longitudinally spaced apart from the unconstrained portion of the second wire.

3. The device of claim 1, wherein the unconstrained portions of the first and second wires are circumferentially spaced from one another about the member.

4. The device of claim 1, wherein the wires are conductive.

5. The device of claim 1, wherein the first and second wires are constrained by and anchored to first and second lumens formed within the member.

6. The device of claim 1, wherein the first and second wires are constrained by and anchored by a plurality of spaced retaining members positioned on the member.

7. The device of claim 1, wherein the distal portions of the first and second wires are anchored at a position that is offset from a longitudinal axis of the member.

8. The device of claim 1, further comprising at least one central working channel extending between proximal and distal ends of the member.

9. A device for cutting tissue, comprising:
   a flexible elongate member having proximal and distal ends;
   a first guide channel extending along at least a portion of the member, the first guide channel having a proximal portion and a distal portion;
   a first tissue-cutting wire having a proximal end disposed within the proximal portion of the first guide channel, and an exposed portion extending between and outside of the proximal and distal portions of the first guide channel;
   a second guide channel extending along at least a portion of the member such that it is angularly spaced along a circumference of the flexible elongate member from the first guide channel, the second guide channel having a proximal portion and a distal portion;
   a second tissue-cutting wire having a proximal end disposed within the proximal portion of the second guide channel, and an exposed portion extending between and outside of the proximal and distal portions of the second guide channel; and an actuator coupled to the proximal ends of the first and second wires and adapted to selectively and individually apply tension to the first and second wires effective to bend the member to expose the wire to which tension is applied in a cutting configuration at the exposed portion of the wire.

10. The device of claim 8, wherein the exposed portion of the first tissue-cutting wire is spaced a distance apart from the exposed portion of the second tissue-cutting wire along a longitudinal axis of the member.

11. The device of claim 8, wherein the exposed portions of the first and second tissue-cutting wires are radially disposed around the circumference of the member.

12. The device of claim 8, wherein the first and second tissue-cutting wires are conductive.

13. The device of claim 8, wherein the first and second guide channels are lumens that are formed in the flexible elongate member.

14. The device of claim 8, wherein each guide channel is formed by a plurality of spaced retaining members.

15. The device of claim 8, further comprising at least one central working channel that extends between the proximal and distal ends of the member.

* * * * *